US012672831B2

(12) United States Patent
De Leo

(10) Patent No.: US 12,672,831 B2
(45) Date of Patent: Jul. 7, 2026

(54) GLUCOSE READING PROJECTION DEVICE AND METHOD

(71) Applicant: John De Leo, Mandeville, LA (US)

(72) Inventor: John De Leo, Mandeville, LA (US)

( * ) Notice: Subject to any disclaimer, the term of this patent is extended or adjusted under 35 U.S.C. 154(b) by 541 days.

(21) Appl. No.: 17/988,621

(22) Filed: Nov. 16, 2022

(65) Prior Publication Data

US 2024/0090853 A1 Mar. 21, 2024

Related U.S. Application Data

(60) Provisional application No. 63/279,898, filed on Nov. 16, 2021.

(51) Int. Cl.
*A61B 5/00* (2006.01)
*G16H 40/67* (2018.01)

(52) U.S. Cl.
CPC .......... *A61B 5/7445* (2013.01); *A61B 5/0004* (2013.01); *A61B 5/002* (2013.01); *A61B 5/0022* (2013.01); *G16H 40/67* (2018.01)

(58) Field of Classification Search
CPC ..... A61B 5/7445; A61B 5/0004; A61B 5/002; A61B 5/0022; G16H 40/67
USPC ......................................................... 345/561
See application file for complete search history.

(56) References Cited

U.S. PATENT DOCUMENTS

| | | | |
|---|---|---|---|
| 10,136,845 | B2 | 11/2018 | Taub et al. |
| D852,772 | S | 7/2019 | Zhang |
| 10,691,308 | B2 | 6/2020 | Bernini et al. |
| 2004/0178910 | A1 | 9/2004 | Egger |
| 2009/0046140 | A1* | 2/2009 | Lashmet ................ G09G 3/002 |
| | | | 348/E13.001 |
| 2010/0004522 | A1 | 1/2010 | Varela |
| 2010/0010330 | A1 | 1/2010 | Rankers et al. |
| 2013/0198685 | A1 | 8/2013 | Bernini et al. |
| 2014/0200426 | A1 | 7/2014 | Taub et al. |

(Continued)

FOREIGN PATENT DOCUMENTS

WO 2018178942 10/2018

OTHER PUBLICATIONS

Dexcom G5 Mobile CGM System-Canada/Dexcom (available at https://www.dexcom.com/en-CA/g5-mobile-canada-en) (visited Oct. 26, 2021).

(Continued)

*Primary Examiner* — Jin Ge
(74) *Attorney, Agent, or Firm* — Garvey, Smith & Nehrbass, Patent Attorneys, L.L.C.; Julia M. FitzPatrick; Vanessa M. D'Souza

(57) ABSTRACT

A portable device for projecting medical data of a patient, including a housing, wireless technology that allows the exchange of data between different electronic devices, a projector that can project a light beam image of the data received from the wireless technology onto a desired surface away from the housing, and a coupler that couples the projector to the housing and enables the projector to tilt and/or swivel and/or rotate so that the location of the projected light beam image can be changed, e.g., to display on a ceiling or desired wall. The medical data projected can be glucose level data. The apparatus enables a person to easily obtain information on their glucose levels when they wake at night without having to access an electronic device to obtain the information.

20 Claims, 17 Drawing Sheets

(56)                     References Cited

U.S. PATENT DOCUMENTS

| | | | | |
|---|---|---|---|---|
| 2018/0176748 A1* | 6/2018 | Kim | .................... | H04L 63/0861 |
| 2020/0408386 A1* | 12/2020 | Heimbrock | ............ | A61G 7/012 |
| 2021/0327575 A1* | 10/2021 | Temkin | .................. | G16H 40/20 |

OTHER PUBLICATIONS

Dexcom G6 Continuous Glucose Monitoring (CGM) System | Zero Fingersticks (available at https://www.dexcom.com/g6-cgm-system) (visited Oct. 26, 2021).
Diabetes CGM Mobile Apps & Software |Dexcom (available at https://www.dexcom.com/apps) (visited Oct. 26, 2021).
Get Eversense CGM System | Eversense CGM (available at https://www.ascensiadiabetes.com/eversense/landing pages/eversense4) (visited Oct. 26, 2021).
Guardian Connect CGM System | World's First Smart CGM-Medtronic (https://www.medtronicdiabetes.com/products/guardian/connect/continuous-glucose-monitoring-system) (visited Oct. 26, 2021).
-NutriSense Continuous Glucose Monitoring (available at https://to.nutrisense.io/cgm?utm_source=google&utm_medium=cpc&utm_campaign=cgm_exact_desktop_troas&utm_adgroup=cgm_sensor&utm_keyword=cgmsensor&utm_adpos=&gclid=EAlalQobChM17762) (visited Oct. 26, 2021).
What is Continuous Glucose Monitoring (CGM)? | FreeStyle Libre Systems (available at https://www.freestyle.abbott/us-en/what-is-cgm.html) (visited Oct. 26, 2021).
Bluetooth chips information (available at https://www.globalspec.com/learnmore/semiconductors/communications_rf_wireless_chips/bluetooth_chips) (visited Nov. 11, 2021).
Bluetooth Technology Basics (2003) (Bluetooth device access guide) (available at https://developer.apple.com/library/archive/documentation/DeviceDrivers/Conceptual/Bluetooth/BT_Bluetooth_Basics/BT_Bluetooth_Basics.html) (visited Nov. 21, 2021).
What is the Nightscout Project (2014 captured page) (current web page available at http://www.nightscout.info/) (visited Jul. 26, 2022).
Nightscout blog entry (posting date states Sep. 16, 2014).
Greg Bardos Blog Entry (posting date states Apr. 8, 2020).
SearchReddit entry (available at https://www.reddit.com/r/dexcom/comments/dyth8f/is_there_a_nightstand_or_desktop_like_an_alarm/) (posting appears to be posted 3 years ago) (last visited Feb. 6, 2023).
What is Bluetooth : Architecture & Its Working (available at https://www.elprocus.com/how-does-bluetooth-work/) (visited Nov. 11, 2021).
Smartro Digital Alarm Clock ( 2020 web page capture) (current web page available at https://smartro.co/products/smartro-digital-projection-alarm-clock-with-weather-station-indoor-outdoor-thermometer-usb-charger-dual-alarm-clocks-for-bedrooms-ac-battery-operated) (visited Oct. 25, 2022).

* cited by examiner

GLUCOSE READING PROJECTION DEVICE AND METHOD

CROSS-REFERENCE TO RELATED APPLICATIONS

This application claims the benefit of and/or priority to U.S. Provisional Patent Application Ser. No. 63/279,898 filed on 16 Nov. 2021, which is hereby incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a device that can receive medical data relating to a patient from a software application on an electronic device (e.g., a smart phone, tablet, computer, etc.) and project the medical data onto a desired surface. More particularly, the present invention relates to a device that can receive glucose level readings, and/or other desired medical data relating to a patient, and project the readings or data onto a ceiling or wall or other desired surface of a bedroom, for example.

2. General Background of the Invention

Patients with certain medical conditions, e.g., diabetes, need to monitor their glucose levels throughout the day. A continuous glucose monitoring sensor including a transmitter (e.g., a Dexcom G6 sensor) can be worn by a patient, and the sensor gathers and transmits glucose level readings throughout the day to a patient's electronic device having a receiver, e.g., a smart phone, tablet, computer, etc. For example, the data gathered by the sensor can be set to automatically be transmitted to a software application (app) (e.g., a Dexcom G6 mobile phone or watch app) on a person's smart phone, smart watch, tablet, computer or other electronic device that can store and process data, e.g., using Bluetooth® technology, that can receive and display the information. Some continuous glucose monitoring sensors, systems, or devices that are currently commercially available are sold under the following trademarks or product names: Dexcom G5/6, Eversense, Guardian Connect, and NutriSense).

Overnight, when a patient is sleeping, the continuous glucose monitoring sensor continues to gather, record, and transmit data on blood glucose levels. Often times, people may not be able to quickly find or access their phones, tablets, computers or other electronic devices that can store and process data when waking during the night. A smart phone, for example, needs to be found in the dark, then a passcode or biometric data needs to be entered to access the phone, and a software application needs to be opened to view glucose readings. Sometimes such an electronic device may inadvertently be left in another room overnight, or a battery of a smart device, e.g., a tablet or smart phone, for example, may die overnight. When needing to find and access the electronic device to get the necessary information, these actions and efforts can cause a person to fully wake up and become alert and not be able to fall back asleep. Additionally, if glucose levels are out of an acceptable range, and if an electronic device cannot be readily found, this can present a dangerous medical situation.

There is a need in the art for a device that can be kept on a nightstand or other location in a bedroom that can receive blood glucose level readings, and/or other medical data, on a patient and project the readings to a desired surface in the bedroom, e.g., on a ceiling or a wall, where the patient can easily see the readings when they wake in the middle of the night, without needing to access an app on a phone, tablet, computer or other electronic device that can store and process data.

There is also a need in the art for a device that can be kept on a nightstand or other location in a bedroom that can continuously and/or automatically receive blood glucose level readings, and/or other medical data, on a patient and project the readings to a desired surface in the bedroom, e.g., on a ceiling or a wall, where the patient can easily see the readings when they wake in the middle of the night, without needing to access an app on a phone, tablet, computer or other electronic device that can store and process data.

There is also a need in the art for a device that can be kept on a nightstand or other location in a bedroom that can receive blood glucose level readings and which is configured to issue an alarm if the blood glucose level readings are not within an acceptable range.

The following U.S. Patents and Patent Publications are incorporated herein by reference:

| Patent No. | TITLE | ISSUE DATE |
|---|---|---|
| 10,136,845 | DEVICES, SYSTEMS, AND METHODS ASSOCIATED WITH ANALYTE MONITORING DEVICES AND DEVICES INCORPORATING THE SAME | Nov. 27, 2018 |
| 10,691,308 | CONTROLLING THE DISPLAY OF A DATASET | Jun. 23, 2020 |
| D852,772 | PROJECTION ALARM CLOCK RADIO | Jul. 2, 2019 |
| 2004/0178910 | PATIENT MONITORING SYSTEM | Sep. 16, 2004 |
| 2010/0004522 | CONTINUOUSLY WEARABLE COMPACT BLOOD GLUCOSE MEASURING DEVICE | Jan. 7, 2010 |
| 2010/0010330 | WIRELESS MONITOR FOR A PERSONAL MEDICAL DEVICE SYSTEM | Jan. 14, 2010 |
| 2013/0198685 | CONTROLLING THE DISPLAY OF A DATASET | Aug. 1, 2013 |
| 2014/0200426 | DEVICES, SYSTEMS, AND METHODS ASSOCIATED WITH ANALYTE MONITORING DEVICES AND DEVICES INCORPORATING THE SAME | Jul. 17, 2014 |
| WO2018/178942 | METHOD AND SYSTEM OF DISPLAYING A REAL-TIME GLUCOSE READING WITH AN ALARM CLOCK | Oct. 4, 2018 |

The following web pages are incorporated herein by reference and being filed herewith.

Dexcom G5 Mobile CGM System-Canada/Dexcom - https://www.dexcom.com/en-CA/g5-mobile-canada-en
Dexcom G6 Continuous Glucose Monitoring (CGM) System | Zero Fingersticks https://www.dexcom.com/g6-cgm-system
Diabetes CGM Mobile Apps & Software | Dexcom - https://www.dexcom.com/apps
Get Eversense CGM System | Eversense CGM -
https://www.ascensiadiabetes.com/eversense /landing pages/eversense4
Guardian Connect CGM System | World's First Smart CGM-Medtronic -
https://www.medtronicdiabetes.com/products/guardian/connect/continuous-glucose-monitoring-system
NutriSense Continuous Glucose Monitoring-
https://to.nutrisense.io/cgm?utm_source=google&utm_medium=cpc&utm_campaign=cg
m_exact_desktop_troas&utm_adgroup=cgm_sensor&utm_keyword=cgmsensor&utm_a
dpos=&gclid=EAlaIQobChM17762
What is Continuous Glucose Monitoring (CGM)? | FreeStyle Libre Systems -
https://www.freestyle.abbott/us-en/what-is-cgm.html
Bluetooth chips information-
https://www.globalspec.com/learnmore/semiconductors/communications_rf_wireless_chips/bluetooth_chips
Bluetooth device access guide-
https://developer.apple.com/library/archive/documentation/DeviceDrivers/Conceptual/Bluetooth/BT_Bluetooth_Basics/BT_Bluetooth_Basics.html

BRIEF SUMMARY OF THE INVENTION

One or more preferred embodiments of the apparatus and method of the present invention solves the problems in the prior art in a simple and straightforward manner. One or more preferred embodiments of the apparatus of the present invention is a device that can receive, display and preferably project medical information onto a surface. In some embodiments the device can also be configured to store medical data or information on a patient. Preferably, the device is adapted to display glucose sensor readings, e.g., received from a continuous glucose monitoring sensor that is currently available on the market or to be developed in the future. The time of day can also be included in a display on the device. The device also preferably projects the glucose reading on a ceiling or wall or other desired surface of a room so that a person can simply open an eye and see their reading at night. The device also preferably is configured to project the time of day onto a ceiling or wall or other desired surface of a room.

The device is preferably equipped with wireless technology that allows the exchange of data between different devices, e.g., Bluetooth® and/or Near Field Communication (NFC) technology. The device can thus contain a Bluetooth chipset equipped with Bluetooth® wireless technology. The Bluetooth® technology included can be the same or similar to that included in Bluetooth® projectors or speakers that are currently on the market. Near Field Communication (NFC) is a branch within the family of RFID technology, and a branch of High-Frequency (HF) RFID. Both operate at the 13.56 MHz frequency. NFC provides a secure form of data exchange, and an NFC device can be used as both an NFC reader and an NFC tag, which allows NFC devices to communicate peer to-peer.

The apparatus and method of the present invention is beneficial to both a diabetic patient and the patient's caregiver. With a combination of glucose display/clock, a person can read on a bedroom ceiling or wall, his or her own current glucose level, or the current glucose level of a family member in another room of the same building, or anywhere in the world, e.g., if the caregiver is following the person's glucose reading thru the Dexcom share app or similar app. This can provide tremendous comfort and relief to parents of diabetic children, adult children caring for diabetic parents, and other caregivers.

In one or more preferred embodiments, the device of the present invention is a small, portable device (e.g., most preferably about 2 inches in height by 2 inches in width by 6 inches, or more preferably 0.8 to 3 inches in height and/or width, and 3 to 8 inches in length), lightweight (e.g., 6 to 12 ounces) and compact so that it can be packed in a purse or small travel bag or back pack or briefcase, and brought anywhere in the world to display the current time and glucose reading of a person.

In one or more preferred embodiments, the device of the present invention can include a battery, a battery backup, and/or an electric cord.

In one or more preferred embodiments, the device of the present invention will include a battery backup, and/or an electric cord.

In one or more preferred embodiments, a device of the present invention can include a port for connecting a power cord.

In one or more preferred embodiments, a device of the present invention can include a power cord manufactured as part of the device.

In one or more preferred embodiments, the device of the present invention can include one or more USB ports, e.g., for charging a cell phone or other electronic device, or for a power cord for charging the device of the present invention itself.

In one or more preferred embodiments, the device of the present invention can be any desired color, e.g., black, purple, pink, blue, red, silver, gray, brown, green, etc., or can have a desired design on an exterior of the device.

Preferably an app used in one or more embodiments of the system of the present invention can be configured to send an alert to the device of the present invention when data is received, and the device is adapted to provide an alert signal, e.g., preferably a desired sound, so that the patient can be made aware that new data is available and check and review the data. Other alert signals can also be chosen if desired, e.g., beeping, flashing lights, and/or vibration. The app preferably can also be configured to provide an alarm transmission to the device if glucose levels are out of an acceptable range, and the device can provide an alarm signal, e.g., preferably a desired sound and/or beeping, that is designed to wake a person from sleep and/or to designate to a person that a glucose reading or data received is out of a desired range. Other alarm signals, e.g., flashing lights, and/or vibration can also be included if desired. Preferably the alarm signal is different from an alert signal so that a person using the device can discern the difference in meaning between the signals provided by the device.

In one or more preferred embodiments, medical data, e.g., glucose readings, are updated at least every 5 minutes. In other preferred embodiments, any desired time interval can be selected for updating medical data, e.g., every 1 to 10 minutes, or in 5 to 55 second intervals for example if desired.

In one or more preferred embodiments of the present invention, the device can be configured to provide an alert when data is received so that the patient can check and review the data. The device can also be configured to provide an alarm if glucose levels are out of an acceptable range. Preferably the alarm is loud enough to wake another person in the same bedroom as the patient or in another room from the patient so that the other person can aid the patient, e.g., depending on how high or low the glucose levels are and whether the patient is unresponsive or unable to take care of or address his or her own needs.

In one or more preferred embodiments, the device can include different light settings, e.g., a low light beam, a medium light beam, and/or a high light beam.

In one or more preferred embodiments, the device can include different light settings, e.g., different colors that the medical data and time will be displayed in. In one or more preferred embodiments, a medical reading can be displayed in one color light and a time reading can be displayed in a different color light.

In one or more preferred embodiments the device includes a projector for projecting and displaying medical data on a desired surface, e.g., a ceiling or a wall.

In one or more preferred embodiments the device includes a projector for projecting and displaying medical data and current time on a desired surface, e.g., a ceiling or a wall.

In one or more preferred embodiments the device includes a projector for projecting and displaying glucose readings and current time on a desired surface, e.g., a ceiling or a wall.

In one or more preferred embodiments, other type of information as desired can be projected, e.g., current date.

In one or more preferred embodiments, other type of information as desired can be displayed, e.g., current date.

In one or more preferred embodiments of the device, the projector is adapted to swivel, e.g., connected to the device with a coupler that can swivel, e.g., a swivel bracket, so that data being projected can move from side to side and be displayed in a desired location in a room.

In one or more preferred embodiments of the device, the projector is adapted to tilt, e.g., connected to the device with atilt bracket, so that data being projected can tilt up and down, and/or left and right, and/or in another desired direction and be displayed in a desired location in a room.

In one or more preferred embodiments of the device, the projector is adapted to swivel and/or tilt, e.g., connected to the device with a with a coupler that can swivel and/or tilt, e.g., a swivel/tilt bracket, so that data being projected can tilt up and down or in another desired direction, or move from side to side or another desired direction, and be displayed in a desired location in a room.

In one or more preferred embodiments the projector is moveable and/or rotatable, so that data being projected can be displayed in a desired location in a room.

In one or more preferred embodiments the lens of a projector is moveable and/or rotatable, so that data being projected can be displayed in a desired location in a room.

In one or more preferred embodiments, the apparatus of the present invention is not an alarm clock.

In one or more preferred embodiments, the apparatus of the present invention is not a clock radio.

In one or more preferred embodiments, a system for projecting medical data of a patient comprises:

a) a projection device having a housing including a first wireless technology that enables the continuous and automatic exchange of data between different electronic devices;

b) an electronic device that includes a second wireless technology that enables the continuous and automatic exchange of data between different electronic devices;

c) the first wireless technology of the housing adapted to receive the data from the electronic device having the second wireless technology;

d) a projector coupled to the housing that can continuously and automatically project a light beam image of the data received by the first wireless technology onto a desired surface that is spaced away from the housing; and e) a coupler that couples the projector to the housing;

wherein the light beam image of the data is continuously and automatically updated to be the most recent data received by the first wireless technology.

In one or more preferred embodiments, the light beam image of the data is continuously and automatically updated to be the most recent data received by the first wireless technology overnight while a person is sleeping, so that when awaking during the night and in the dark, for example, all a person has to do is look at the ceiling or a wall or other surface where the light beam image of the medical data is projected to see the most current reading.

In one or more preferred embodiments of the system of the present invention, the electronic device has a software application that receives the data from a medical device worn by a patient and then transmits the data to the projection device.

In one or more preferred embodiments of the system of the present invention, the software application is adapted so that it can be set to remain open for a desired time interval so that the continuous and automatic transfer of data from the medical device to the software app and from the software app to the projection device can occur during the time interval.

In one or more preferred embodiments of the system of the present invention, the software application is adapted so that it can always be open so that the continuous and automatic transfer of data from the medical device to the software app and from the software app to the projection device can occur, e.g., all night while a person sleeps.

In one or more preferred embodiments, a method of the present invention is for projecting an image of medical data of a patient and includes the following steps:

a) linking a projection device that acts as a receiver with an electronic device that acts as a transmitter, wherein, i) the projection device has a housing including a first wireless technology that enables the continuous and automatic exchange of data between different electronic devices; and ii) the electronic device includes a second wireless technology that enables the continuous and automatic exchange of data between different electronic devices;

b) transmitting data from the electronic device to the projection device continuously and automatically at desired intervals;

d) projecting the data received by the projection device onto a surface spaced away from the projection device;

e) updating the data that is projected by the projection device continuously and automatically to correspond to the most current data received by the projection device.

In one or more preferred embodiments of the method of the present invention, the electronic device includes a software application that receives the data from a medical device worn by a patient, and the software application transmits the data to the projection device. The transmission of data from the medical device to the software app of the electronic device and from the software app to the projection device can be automatic and continuous if the projection device, electronic device and medical device are within range of each other so that the wireless technology and/or sensors of the devices will work to transfer the data between the devices. This can be for example within a 5 to 10 meter range for some Bluetooth® technology, for example.

In one or more preferred embodiments of the method of the present invention, the software application is adapted to be kept open for desired time intervals to enable the continuous and automatic transmission of data and updated projected readings for desired time intervals between desired electronic devices.

In one or more preferred embodiments of the method of the present invention, the projection device receives the data from a medical device worn by a patient. The transmission of data from the medical device to the projection device can be automatic and continuous if the projection device and medical device are within range of each other and turned on so that the wireless technology and/or sensors of the devices will work to transfer the data between the devices. This can be for example within a 5 to 10 meter range for some Bluetooth® technology, for example. A person not in range of the projection device can also view updated information through an electronic device with a software app that can also be updated with the readings from the medical device.

In one or more preferred embodiments, the projector can be coupled to the housing with a coupler that enables the projector to move so that the location of the projected light beam image can be changed.

In one or more preferred embodiments, the projector can be coupled to the housing with a coupler that enables the projector to tilt and/or swivel and/or rotate so that the location of the projected light beam image can be changed.

In one or more preferred embodiments, the data includes glucose level data.

In one or more preferred embodiments, the wireless technology can be Bluetooth® technology including a chipset.

In one or more preferred embodiments, the wireless technology receives the data from a medical device worn by the patient.

In one or more preferred embodiments, the wireless technology receives the data from a software application on the electronic device, which receives the data from a medical device worn by the patient.

In one or more preferred embodiments, the invention includes an alarm that can be emitted if data received is not within a desired range.

In one or more preferred embodiments, the invention includes an alert that is emitted when new data is received.

In one or more preferred embodiments, the alert can be different from the alarm.

In one or more preferred embodiments, the device can be portable.

In one or more preferred embodiments, the device includes a screen to also display the data and/or other desired information.

In one or more preferred embodiments, the device includes a screen to also display the data and time.

In one or more preferred embodiments, the device can display data on a patient that is not in the same room.

In one or more preferred embodiments, the device can display data on a patient that is not in the same building.

In one or more preferred embodiments, a system for projecting medical data of a patient includes:

a) a projection device that can be a receiver having a housing including a first wireless technology that enables the continuous and automatic exchange of data between different electronic devices;

b) an electronic device that can be a transmitter and can also be a receiver that includes a second wireless technology that enables the continuous and automatic exchange of data between different electronic devices;

c) the first wireless technology of the housing adapted to receive the data from the electronic device having the second wireless technology;

d) a projector coupled to the housing that can continuously and automatically project a light beam image of the data received by the first wireless technology onto a desired surface that is spaced away from the housing; and e) a coupler that couples the projector to the housing;

wherein the light beam image of the data is continuously and automatically updated to be the most recent data received by the first wireless technology.

In one or more preferred embodiments, the electronic device can have a software application that receives the data from a medical device worn by a patient and then transmits the data to the projection device.

In one or more preferred embodiments, the software application can be adapted so that it can be set to always remain open for a desired time interval so that the continuous and automatic transfer of data from the medical device to the software app and from the software app to the projection device can occur.

In one or more preferred embodiments, the software application can be adapted so that it can always be open so that the continuous and automatic transfer of data from the medical device to the software app and from the software app to the projection device can occur.

In one or more preferred embodiments, a method for projecting an image of medical data comprising the following steps:

a) linking a projection device that acts as a receiver with a transmission device, wherein, i) the projection device has a housing including a first wireless technology that enables the continuous and automatic exchange of data between different devices; and ii) the transmission device includes a second wireless technology that enables the continuous and automatic exchange of data between different devices;

b) transmitting data from the transmission device to the projection device continuously and automatically at desired intervals;

c) projecting the data received by the projection device onto a surface spaced away from the projection device;

d) updating the data that is projected by the projection device continuously and automatically at desired time intervals to correspond to the most current data received by the projection device.

In one or more preferred embodiments, the transmission device includes a software application that receives the data from a medical device worn by a patient.

In one or more preferred embodiments, the software application can be adapted to be kept open for desired time intervals to enable the continuous and automatic transmission of data and updated projected readings for desired time intervals.

In one or more preferred embodiments of the present invention, the transmission device can be a medical device worn by a patient.

In one or more preferred embodiment of the present invention, User/Device process flow includes the following:
Device power on.
On boarding prompt to pair with application and user's local router.
Establish connectivity with cloud/nightscout servers (or cloud/desired software application server) and local devices.
Sign up for Nightscout server url (allows viewership of real time data in addition to the projector display) (or signup for server url of a desired software application)
Connect glucose sensors to the device via bluetooth or Wi-Fi
Toggle and interact with user menu screen and device management screen
Display the desired CGM device from anywhere inside the user's home as long as Wi-Fi connection is established.

BRIEF DESCRIPTION OF THE SEVERAL
VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE
INVENTION

Figures 19, 20:
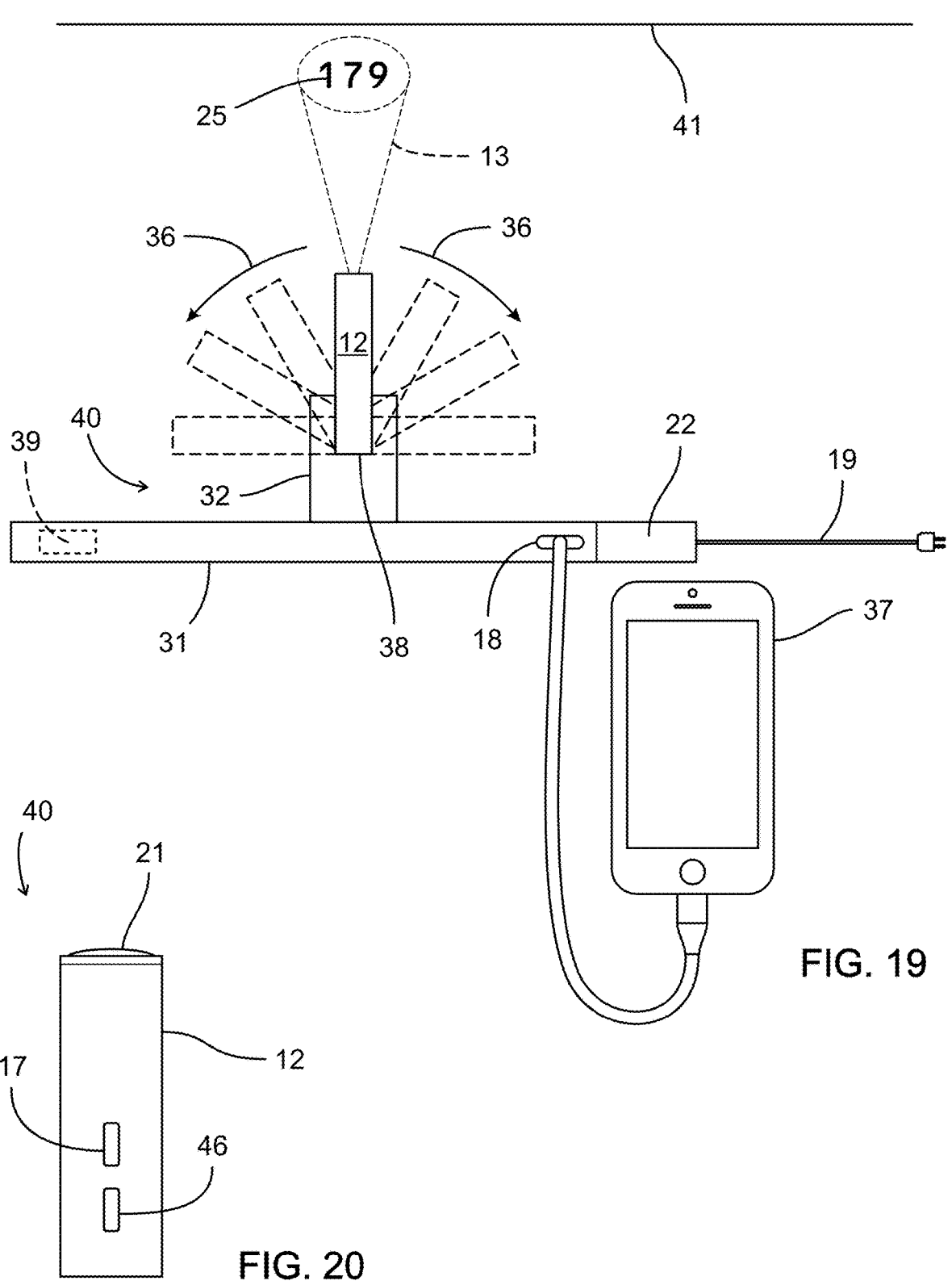
FIG. 19 is a perspective view of a third preferred embodiment of the apparatus of the present invention.
FIG. 20 is a detail view of a projector of the third preferred embodiment of the apparatus of the present invention.
Figure 21:
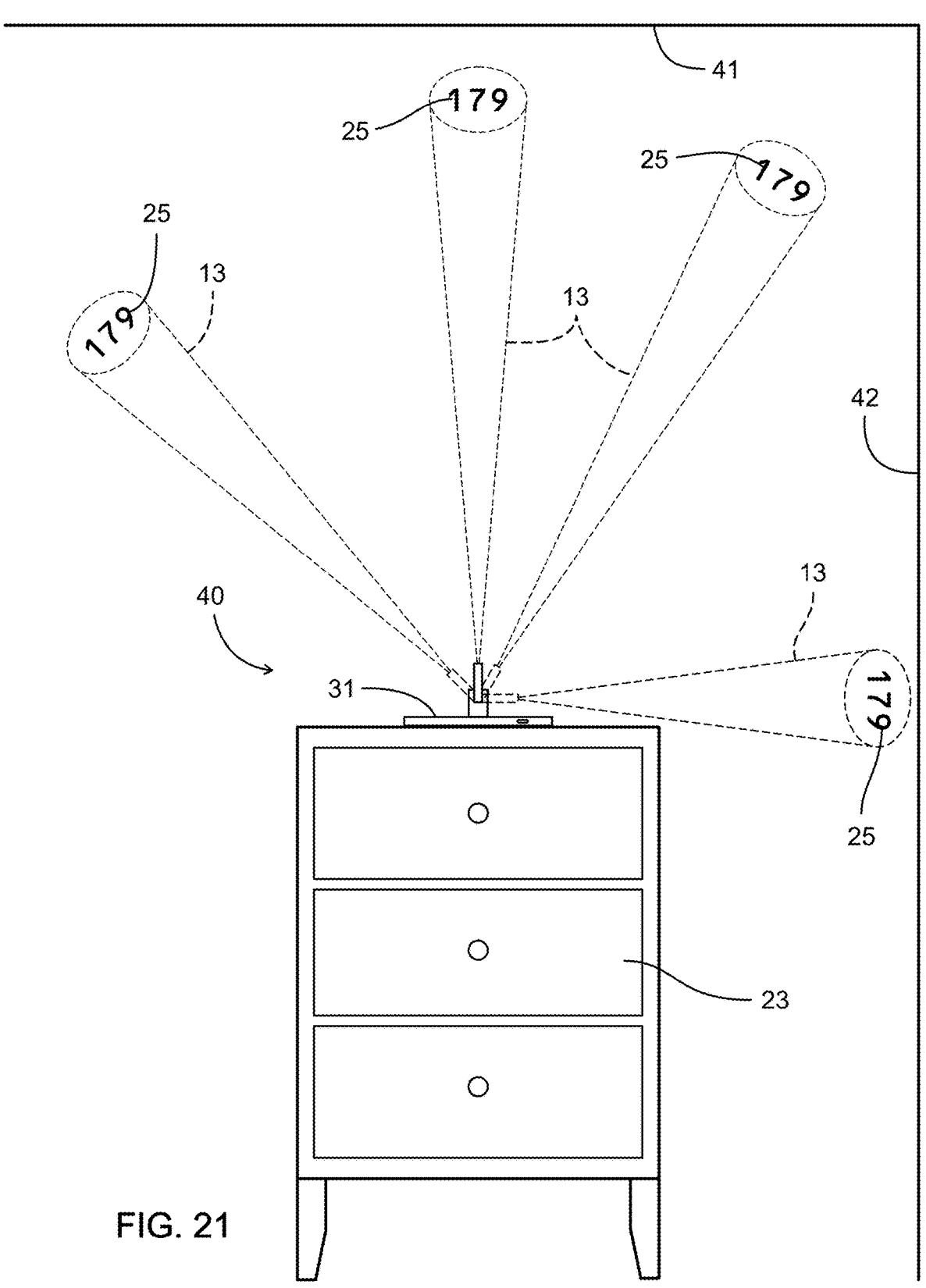
FIG. 21 illustrates the third preferred embodiment of the apparatus of the present invention on a nightstand or bed side table.

FIGS. 1-11 illustrate a first preferred embodiment of the apparatus of the present invention, designated generally by the numeral 10, which includes a projector for projecting and displaying a glucose reading and/or time on another surface, wherein the projector can tilt in a desired direction, e.g., forward, backwards, left and right along a longitudinal axis, to adjust the location of the projected display. FIGS. 12-18 illustrate a second preferred embodiment of the apparatus of the present invention, designated generally by the numeral 30, which includes a projector for projecting and displaying a glucose reading and/or time on another surface, wherein the projector can tilt in a desired direction and also swivel and/or rotate right and left to adjust the location of the projected display. FIGS. 19-21 illustrate a third preferred embodiment of the apparatus of the present invention, designated generally by the numeral 40, which includes a projector for projecting and displaying a glucose reading and/or time on another surface that can tilt in left and right directions along a longitudinal axis to adjust the location of the projected display.

Figure 1:
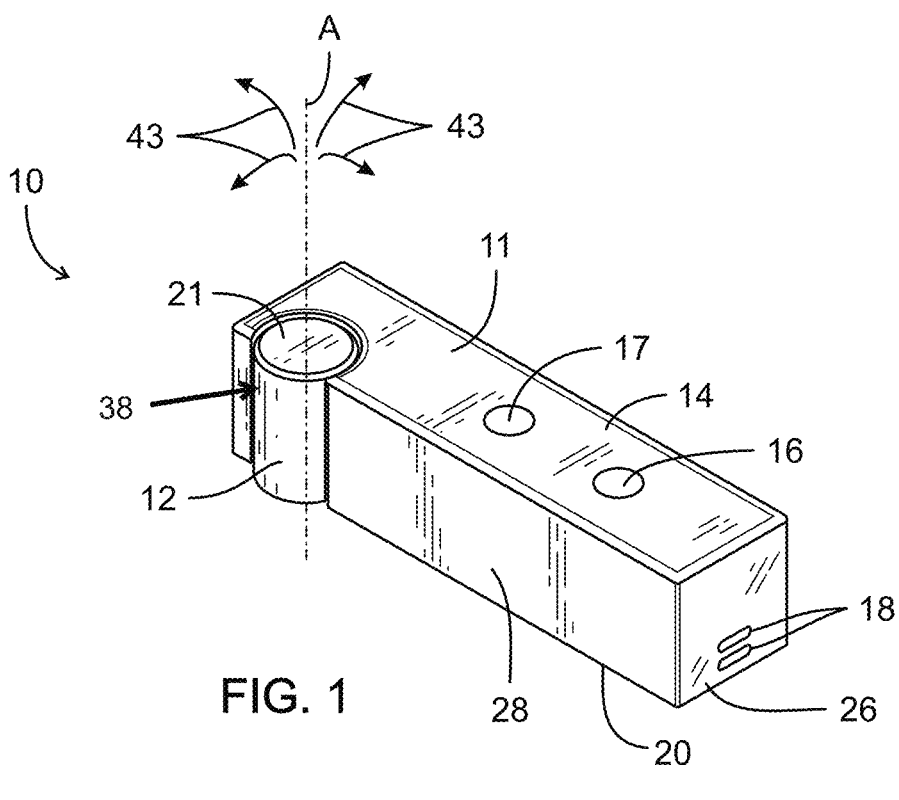
FIG. 1 is a back perspective view of a first preferred embodiment of the apparatus of the present invention.
Figure 2:
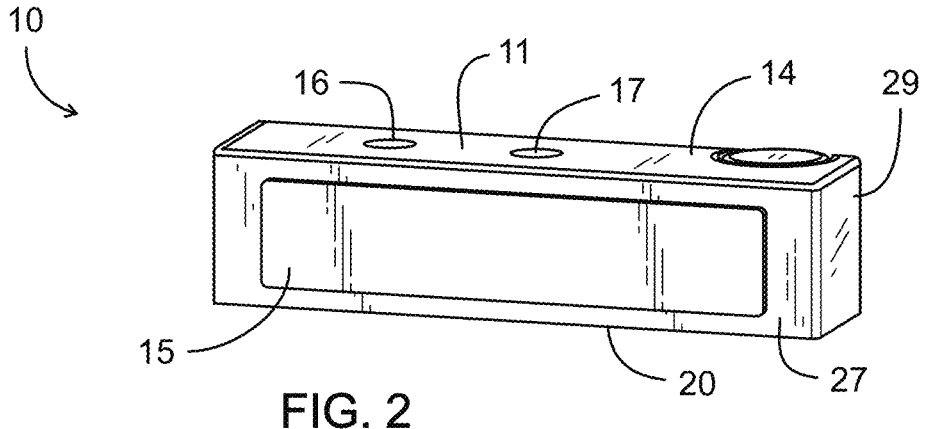
FIG. 2 is a front perspective view of the first preferred embodiment of the apparatus of the present invention.
Figure 3:
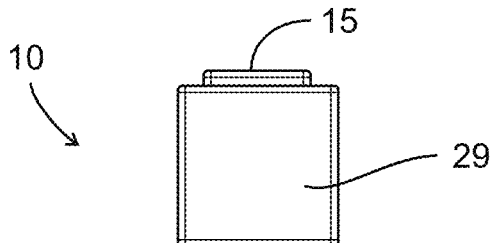
FIG. 3 is a right side view of the first preferred embodiment of the apparatus of the present invention as shown in FIG. 2.
Figure 4:
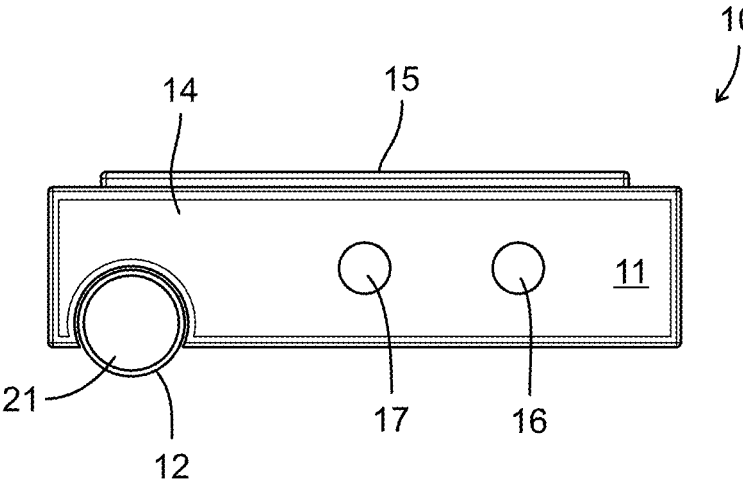
FIG. 4 is a top view of the first preferred embodiment of the apparatus of the present invention as shown in FIGS. 1-2.
Figure 5:
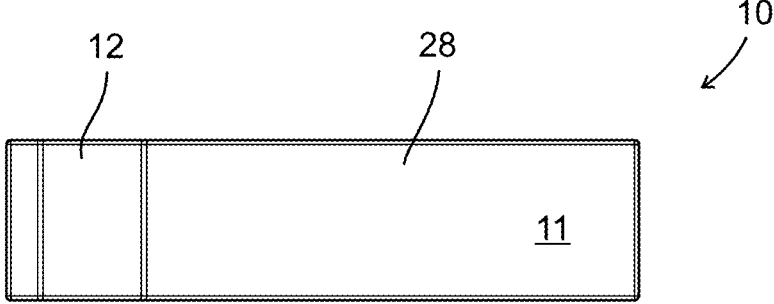
FIG. 5 is a back side view of the first preferred embodiment of the apparatus of the present invention as shown in FIG. 1.
Figure 6:
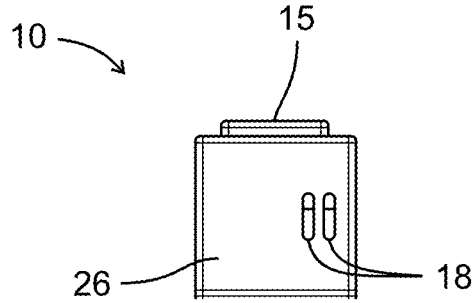
FIG. 6 is a left side view of the first preferred embodiment of the apparatus of the present invention as shown in FIG. 1 including two USB ports.

Referring to FIGS. 1-11, a first preferred embodiment of the apparatus of the present invention designated generally by the numeral 10 is shown. Apparatus 10 is sometimes referred to herein as a projection device, a glucose reading projection device, and/or as a medical data projection device and is adapted to project data, e.g., time and/or medical information, e.g., glucose readings, onto a surface, e.g., a wall or ceiling of a room. A projection device 10 preferably includes a body or base or housing 11 having a top 14, bottom 20, front side 27, back side 28, left side 26 and right side 29. A projector 12 with lens 21 can be included within housing 11, e.g., at least partially within housing 11 as shown in FIG. 1, for example. A light beam 13 can project from projector 12 to display a light beam image on another surface, e.g., wall 42 or ceiling 41. A light beam image can be medial data 25 or time 24, for example.

Figure 7:
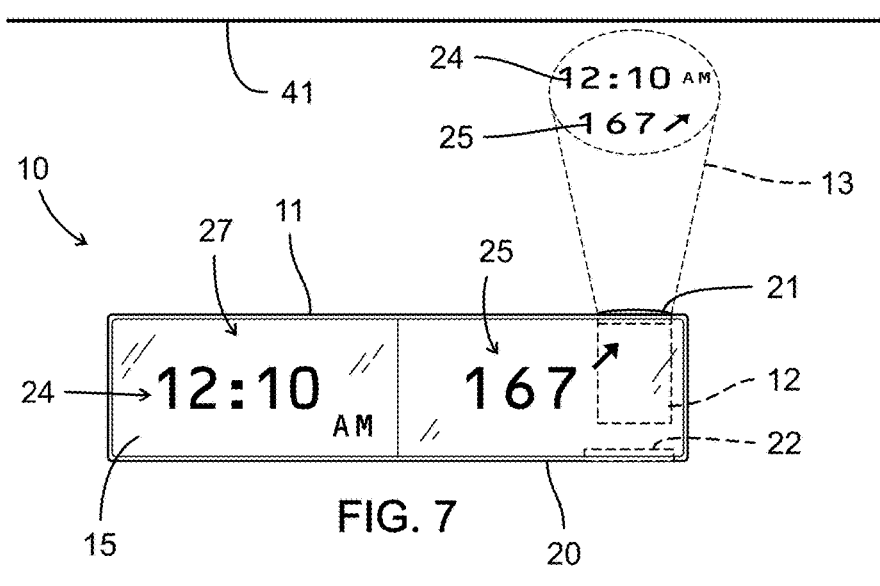
FIG. 7 is a front side view of a first preferred embodiment of the apparatus of the present invention including a battery backup.
Figure 8:
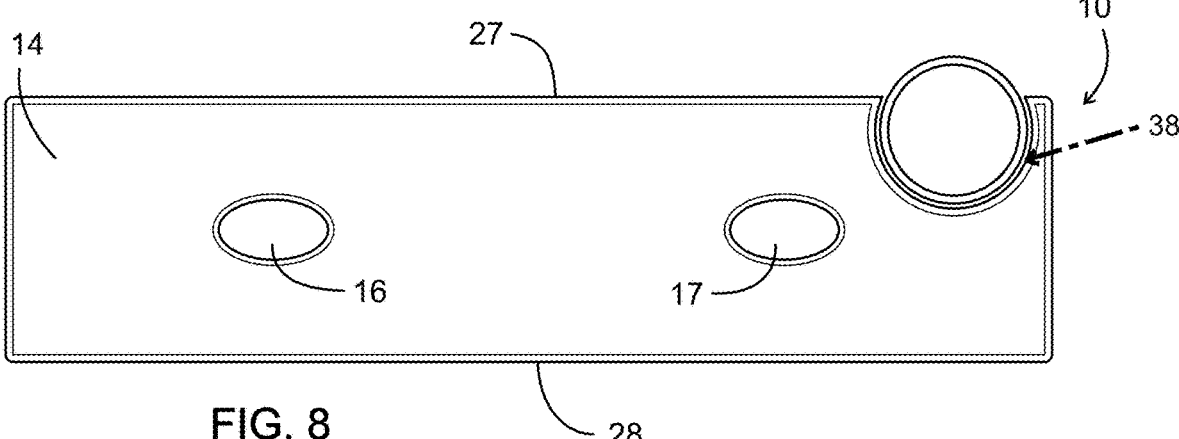
FIG. 8 is a top view of the first preferred embodiment of the apparatus of the present invention.
Figures 9, 10:
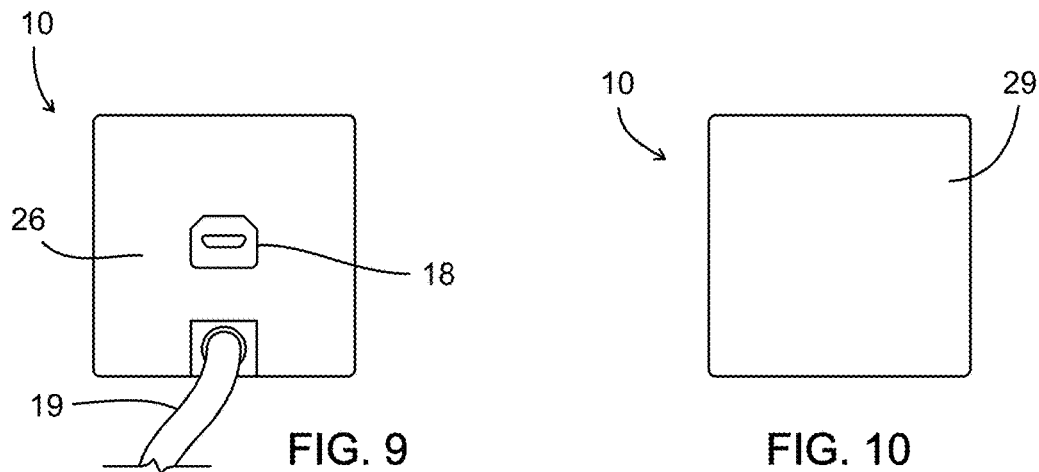
FIG. 9 is left side view of a variation of the first preferred embodiment of the apparatus of the present invention including a power cord and a micro USB port.
FIG. 10 is a right side view of the first preferred embodiment of the apparatus of the present invention.

A screen 15 can be on housing 11 of projection device 10 for displaying medical data 25 received from another device collecting medical data on a patient, e.g., a continuous glucose monitoring sensor worn by a patient that has a sensor and transmitter. Screen 15 can also display time 24 information if desired. Housing 11 can include one or more ports 18 for connecting a cord, e.g., a USB port, at a desired location, e.g., on a side of housing 11, e.g., on a left side 26 (see FIGS. 6, 9). Housing 11 can also include a power cord 19 (e.g., as shown in FIG. 9) and/or a battery backup 22 (e.g., as shown in FIG. 7).

Projection device 10 is a device that can receive and project medical information. Projection device 10 can also be adapted to store (including a computer or computer memory device or programmable logic controller) and display data if desired. Preferably, projection device 10 is adapted to display medical readings, e.g., glucose sensor readings 25, e.g., received from a continuous glucose monitoring sensor that is currently available on the market or to be developed in the future. The time of day 24 can also be included in a display on the device and/or as part of a projected reading. A device 10 also preferably projects the glucose reading 25 on a ceiling 41 or wall 42 or other desired surface of a room so that a person can simply open an eye and see their reading at night. A device 10 also preferably is configured to project the time of day 24 onto a ceiling 41 or wall 42.

Housing 11 is preferably equipped with wireless technology that allows the exchange of data between different devices, e.g., Bluetooth® and/or Near Field Communication (NFC) technology, so that the wireless technology in housing 11 can receive medical data 25 (e.g., a glucose reading from a continuous glucose monitoring sensor worn by a person or from a software application that receives medical data from device worn by a person), and send the medical data to a projector that can project the medical data 25 away from housing 11 onto a surface, e.g., a ceiling 41 or wall 42 or other surface that may be in a bedroom, for example. Device 10 also preferably displays the medical data 25 on a screen 15 as well.

Figure 11:
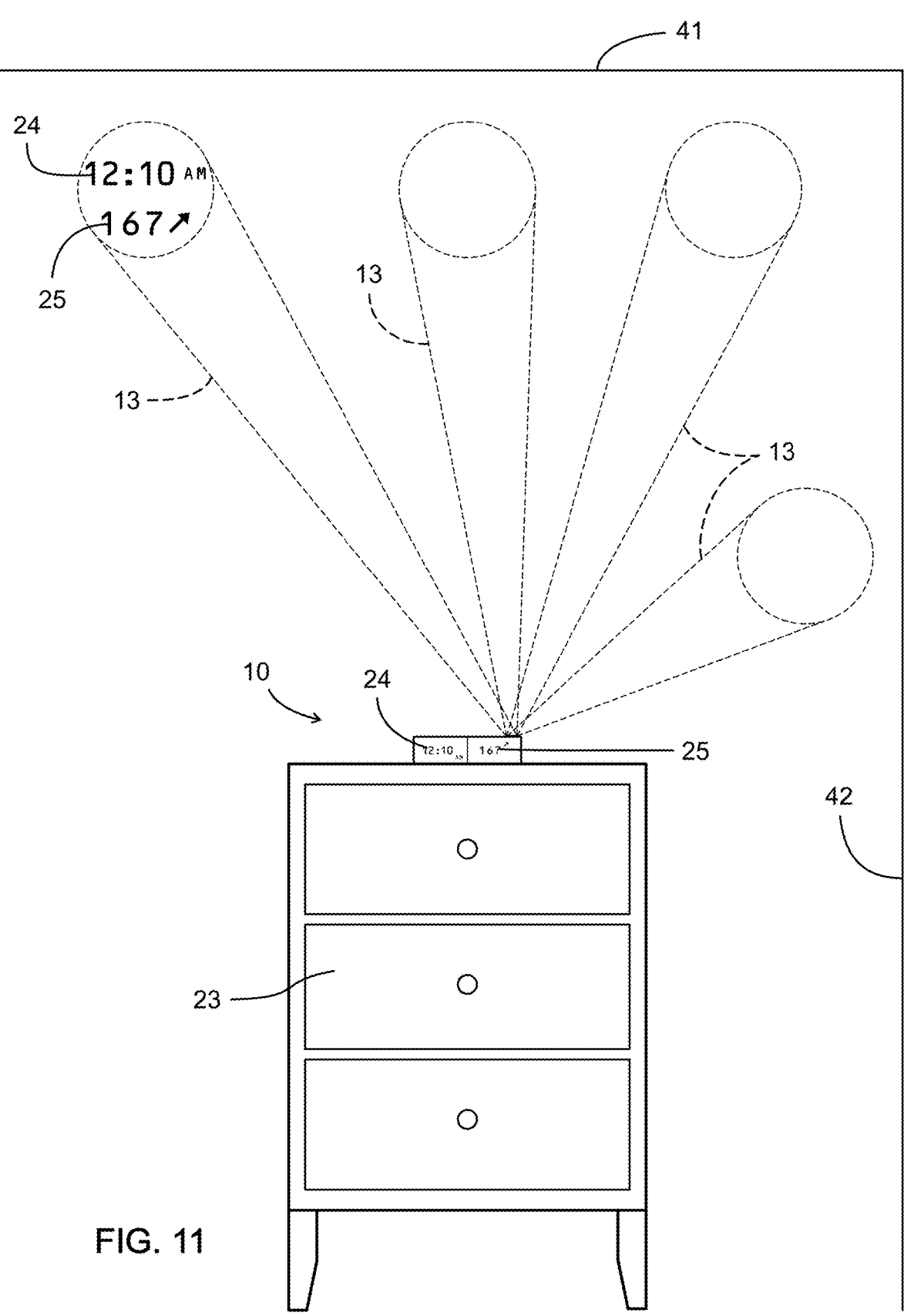
FIG. 11 illustrates the first preferred embodiment of the apparatus of the present invention on a nightstand or bed side table.
Figure 12:
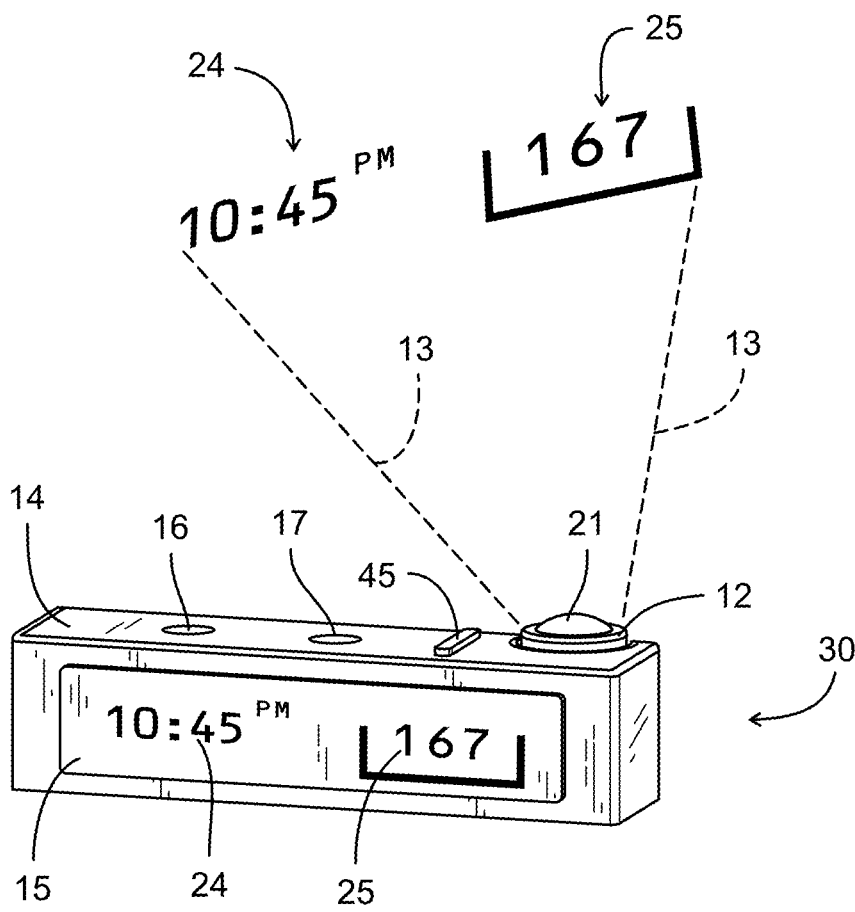
FIG. 12 is a front perspective view of a second preferred embodiment of the apparatus of the present invention.
Figure 13:
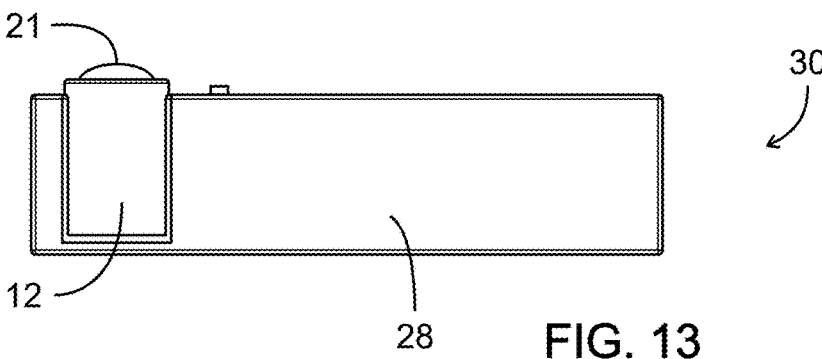
FIG. 13 is a back side view of the second preferred embodiment of the apparatus of the present invention.
Figure 14:
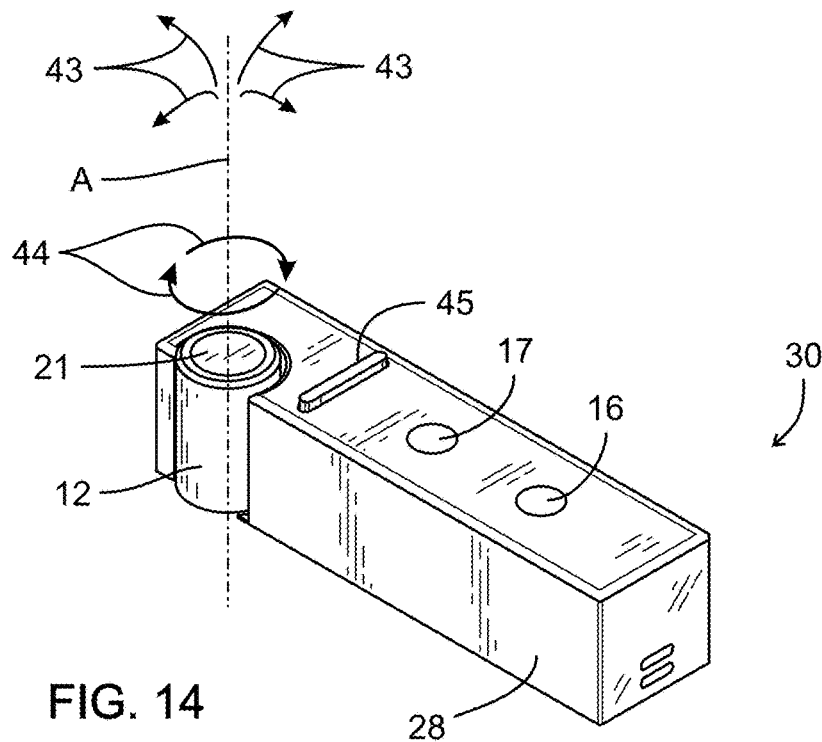
FIG. 14 is a back perspective view of the second preferred embodiment of the apparatus of the present invention.
Figure 15:
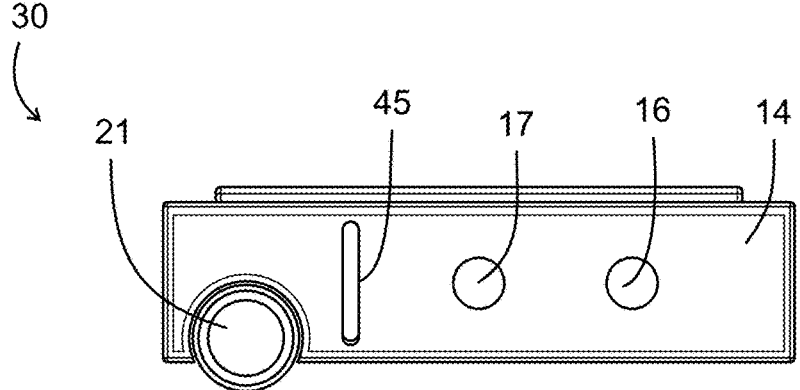
FIG. 15 is a top view of the second preferred embodiment of the apparatus of the present invention.
Figure 16:
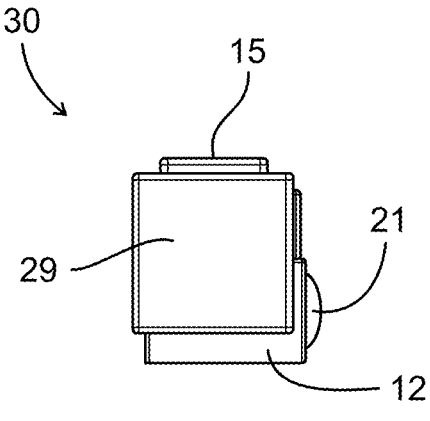
FIG. 16 is a right side view of the second preferred embodiment of the apparatus of the present invention.
Figure 17:
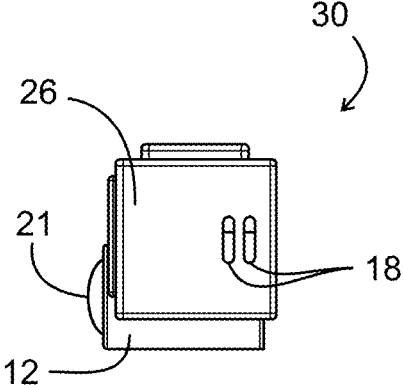
FIG. 17 is a left side view of the second preferred embodiment of the apparatus of the present invention.
Figure 18:
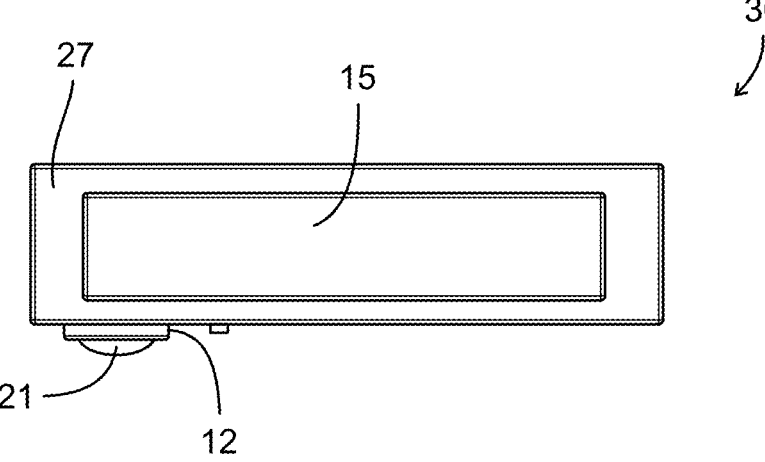
FIG. 18 is a front view of the second preferred embodiment of the apparatus of the present invention as shown in FIG. 12, oriented upside down.

Projector 12 in this embodiment preferably is installed in, or partially, within housing 11 with a coupler 38, e.g., a bracket connection that enables projector 12 to tilt in the direction of arrows 43 along a longitudinal axis "A", e.g., in a forward and backwards direction and also in a left and right direction of housing 11. This tilt function enables an image of medical data 25 and/or time 24 to be projected away from housing 11 at a desired angle, e.g., at an angle of, or in between, 0 to 40 degrees, or possibly at an angle of or between 0 and 180 degrees. This enables medical data 25 and/or time 24 to be displayed at a desired location in a room on a wall 42 or ceiling 41, or other surface, that is easily in view of a person when they awake during the night. FIG. 11 illustrates projection device 10 on a nightstand 23 showing different possible projection light beams 13 as projector 12 moves left and right in a direction of arrows 43. A lens 21 of a projector 12 can be adapted to rotate or swivel, if desired.

Preferably projection device 10 is small and of a size that can easily fit in a purse, or backpack, or briefcase, or travel bag, for example, so it can easily be taken with a person while traveling or away from home. Some preferred dimensions of projection device 10 are shown in FIGS. 1-6, e.g., about 1.4 inches wide, by 1.4 inches tall, by 5.8 inches long. A device 10 can also be about 2 inches wide by 2 inches tall by 6 inches long, for example.

In one or more preferred embodiments projection device 10 is equipped with wireless technology enabling it to receive information or data from a software app. In one or more preferred embodiments, more than one or multiple projection devices 10 can receive the same information or data, which can be in real time, from a software app. This enables more than one projection device 10 to receive and project the same medical data on a patient in more than one location. One such projection device 10 can be in the bedroom of a child for example, while the other projection device 10 can be in the bedroom of a parent in the same household. Or, for example, one such projection 10 can be in a hotel room with a person while traveling, with another such projection device 10 in a bedroom of a spouse or parent of the traveling person's home.

In the figures, projector 12 is shown partially within housing 11. In other embodiments, projector 12 can be coupled at a side of housing 11 instead, which can enable a greater range of tilt movement, for example, in desired directions.

Referring to FIGS. 12-18, a second preferred embodiment of the apparatus of the present invention designated generally by the numeral 30 is shown. Apparatus 30 is sometimes referred to herein as a projection device, a glucose reading projection device, and/or as a medical data projection device.

As shown in the figures, projection device 30 can be the same or similar to projection device 10. In device 30, projector 12 has a bracket or other coupler that also enables projector 12 to swivel or rotate along longitudinal axis "A" in right and left directions, e.g., in the direction of arrows 44, e.g., rotate 90 degrees to the right or left. It is also possible that projector 12 could rotate 360 degrees along longitudinal axis "A" if desired. In this embodiment, the bracket or coupler 38 of projector 12 can also be adapted to allow projector 12 to move or tilt in the direction of arrows 43 along a longitudinal axis "A", e.g., tilt in a forward and backwards direction and also to tilt in left and right directions of housing 11, to enable the medical data 25 and/or time 24 to be projected away from housing 11 at a desired angle, e.g., at an angle of, or in between, 0 to 90 degrees, or possibly at an angle of, or in between, 0 and 180 degrees.

A projection device 30 also preferably is equipped with wireless technology as described in one or more embodiments with regard to projection device 10.

Referring to FIGS. 19-21, a third preferred embodiment of the apparatus of the present invention designated generally by the numeral 40 is shown. Apparatus 40 is sometimes referred to herein as a projection device, a glucose reading projection device, and/or as a medical data projection device.

Projection device 40 includes a base, stand or housing 31, which can be equipped with wireless (e.g., Bluetooth®) technology (represented schematically by the numeral 39), or other desired wireless technology that allows the transfer of data between electronic devices, a battery backup 22, and a USB port 18, or other port to attach a desired cord. Projection device 40 preferably includes firmware or software 49 (not shown) enabling one or more embodiments of the process of the present invention to be carried out. Power cord 19 can also be included with projection device 40. In this embodiment, a display screen 15 is not included on the projection device 40, which just has a projector 12 coupled in projector holder 32. Projector 12 preferably is coupled in holder 32 with bracket or coupler 38 that enables projector 12 to at least tilt in left and right directions (see arrows 36 of, e.g., FIG. 19) to adjust the location of a projected light beam 13 on a ceiling 41 or wall 42 where an image of medical data 25, e.g., a glucose reading received from a continuous glucose sensor worn by a person or from a software app receiving data from a continuous glucose sensor worn by a person, can be displayed.

A projection device 40 also preferably is equipped with wireless technology 39 as described in one or more embodiments with regard to projection device 10. Coupler or bracket 38 of projection device 40 can also be adapted to enable projector 12 to tilt in other directions if desired, and/or to rotate or swivel. A lens 21 of projector 12 can also be adapted to rotate or swivel.

In one or more preferred embodiments, projection device 40 can include one or more USB ports 18, e.g., for charging a cell phone 37 or other electronic device, or for a power cord for charging the device 40 itself.

Figure 22:
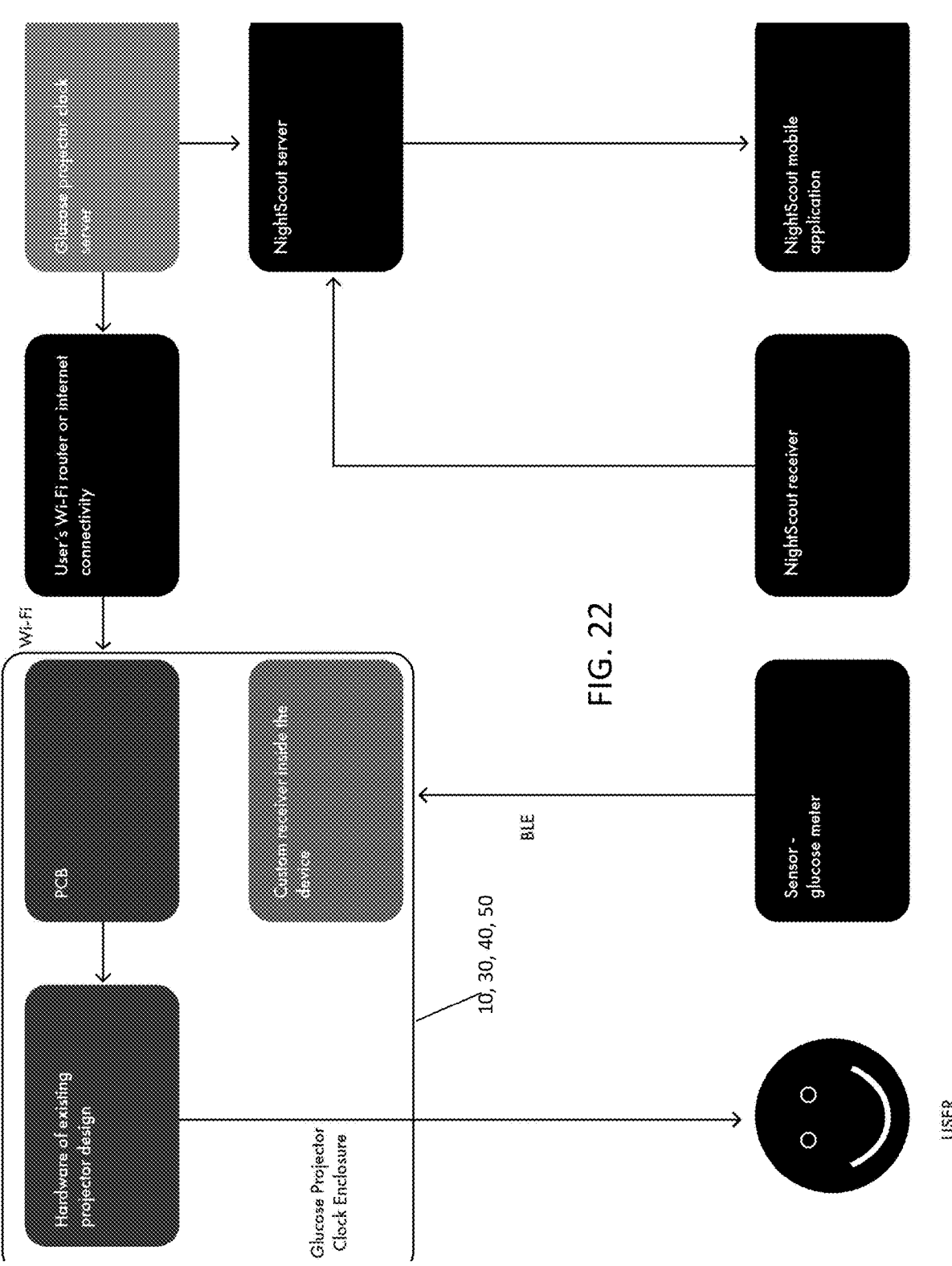
FIG. 22 is a flow chart setting forth steps of a method of a preferred embodiment of the present invention and showing components of a system in a preferred embodiment of the present invention.
Figure 23:
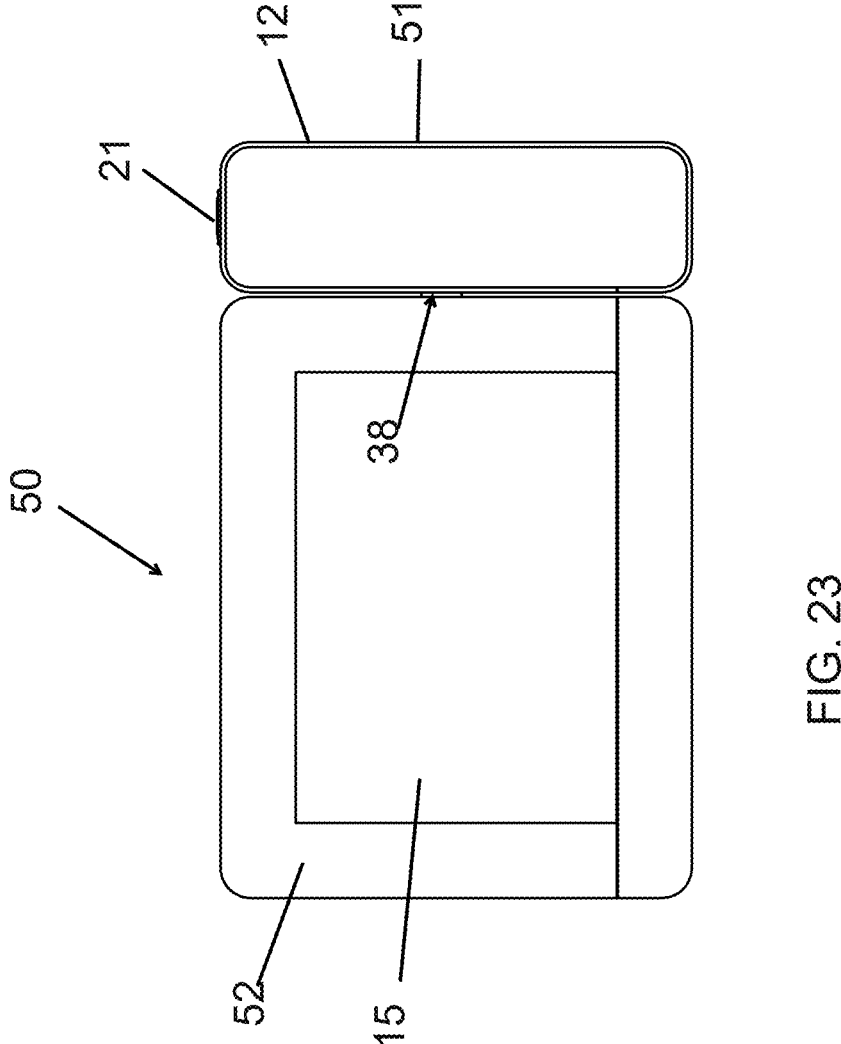
FIG. 23 is a front view of a fourth preferred embodiment of the apparatus of the present invention.
Figure 24:
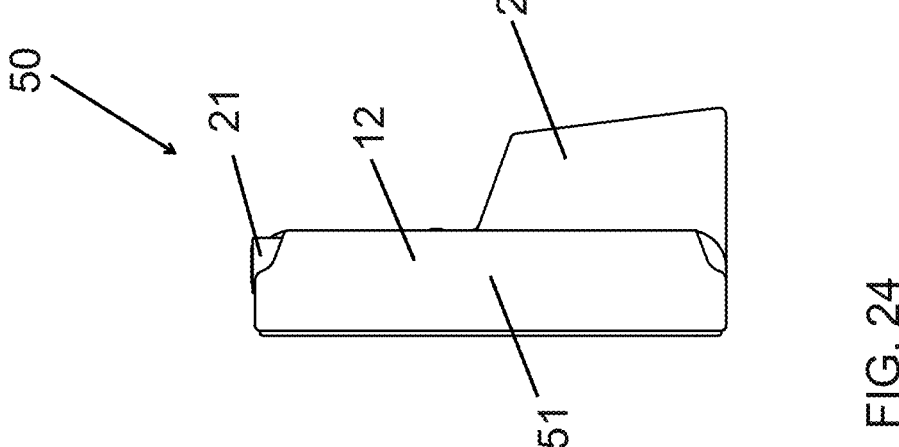
FIG. 24 is a right side view of a fourth preferred embodiment of the apparatus of the present invention.

FIG. 22 is a flow chart depicting components of a preferred embodiment of a glucose projection device system and steps in a preferred embodiment of the method. A device, 10, 30, 40, 50 can include a projector 21 with hardware therein adapted to enable the projector to project an image received from a custom receiver in the device. A device 10, 30, 40, 50 can also include a Printed Circuit Board (PCB) and firmware enabling the device 10, 30, 40, 50 to function as described in one or more embodiments set forth herein.

A user's/patient's real time blood glucose information can be sensed by a glucose sensor. The information can be sent from the glucose sensor to a software application's receiver, e.g., a Nightscout™ receiver, which is sent to a server, e.g., a Nightscout™ server, which is sent to a software application that can be downloaded on a smart device, e.g., a user's phone 37.

A device 10, 30, 40, 50 can be connected to a user's/patient's Wi-Fi that is also in communication with a server of device 10, 30, 40, 50. A server of device 10, 30, 40, 50 can receive information from the software app of the user's smart device, which can be sent to the receiver within the projection device 10, 30, 40, 50 and sent to projector 12 to project the information onto a surface, where the user can view the information, e.g., about glucose levels.

If desired, a glucose sensor of the user/patient can also be in direct communication with the device 10, 30, 40, 50, e.g., using Bluetooth Low Energy (BLE) technology.

A family member or friend of a user/patient, or other third party, can have their own projection device 10, 30, 40, 50. The family member or friend or other third party generally would not have the glucose sensor in proximity to their projection device 10, 30, 40, 50, but they can still receive real time information from the sensor via a software application on their phone that is in communication with the glucose sensor server and in communication in a same or similar manner with their own projection device 10, 30, 40, 50 as shown in FIG. 22.

Thus, one, two, three, four or any desired number of devices 10, 30, 40, 50, with or without a glucose sensor in the device's proximity, can project the same real time glucose information received from a glucose sensor worn by a user/patient. This can occur with the different devices 10, 30, 40, 50 being in different rooms of a same household or building, in different buildings, in different cities, in different states, or in different countries, all at the same time with the different users each having projected viewable access to the same real time glucose information of the user/patient.

In one or more preferred embodiments of the method of the present invention a User/Device process flow for a user/patient having a glucose sensor can include the following:

Device 10, 30, 40, 50 power on.

On boarding prompt to pair with application and user's local router.

Establish connectivity with cloud/nightscout servers (or with cloud/desired software application servers) and local devices.

Sign up for Nightscout server url (allows viewership of real time data in addition to the projector display) (or sign up for a desired software application server url)

Connect glucose sensors to the device via bluetooth or Wi-Fi

Toggle and interact with user menu screen and device management screen

Display the desired information for a Continuous Glucose Monitoring (CGM) device 10, 30, 40, 50 from anywhere inside the user's home or desired building or location as long as Wi-Fi connection is established.

In one or more preferred embodiments of the method of the present invention a User/Device process flow for a user/friend/family member/third party not having a glucose sensor can include the following:

Device 10, 30, 40, 50 power on.

On boarding prompt to pair with application and user's local router.

Establish connectivity with cloud/nightscout servers (or with cloud/desired software application servers) and local devices.

Sign up for Nightscout server url (allows viewership of real time data in addition to the projector display) (or sign up for a desired software application server url)

Toggle and interact with user menu screen and device management screen

Display the desired information for a Continuous Glucose Monitoring (CGM) device 10, 30, 40, 50 from anywhere inside the user's home or desired building or location as long as Wi-Fi connection is established.

FIGS. 23-29 illustrate a fourth preferred embodiment of the apparatus of the present invention, or a projection device 50. An appendix to the specification also includes various views (numbered as FIGS. 30-103) of different variations of the fourth preferred embodiment of the apparatus of the present invention, or a projection device, designated generally as the number 50.

Figure 25:
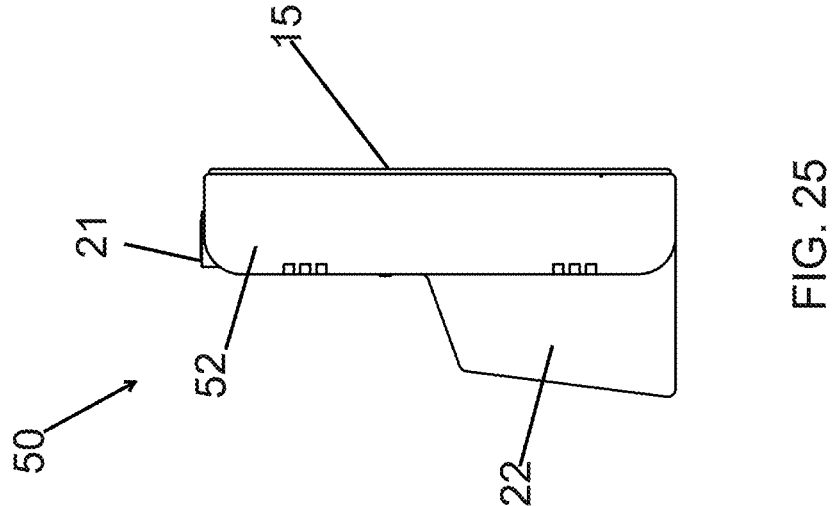
FIG. 25 is a left side view of a fourth preferred embodiment of the apparatus of the present invention.
Figure 26:
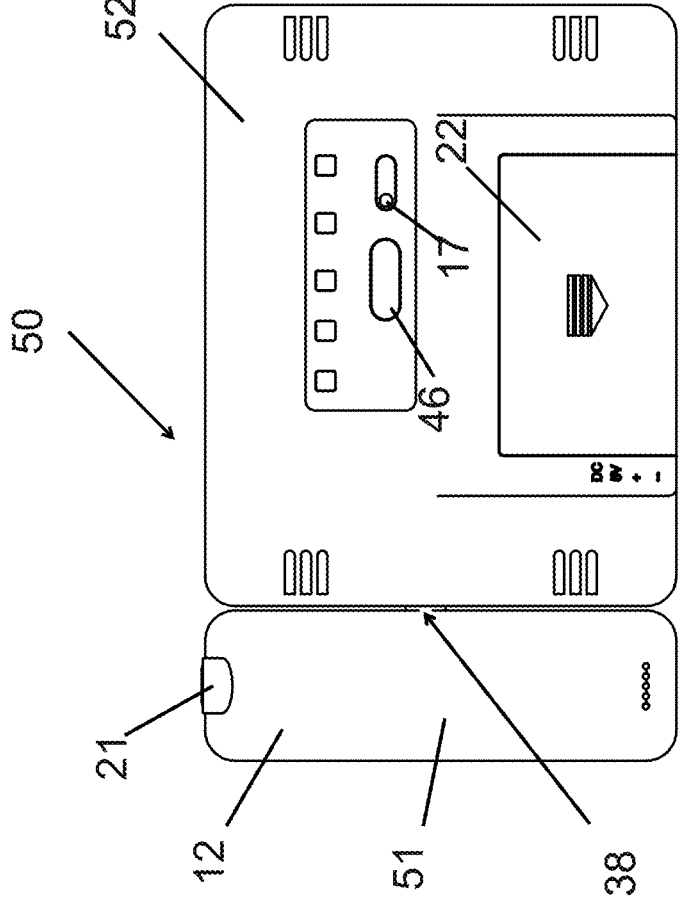
FIG. 26 is a back view of a fourth preferred embodiment of the apparatus of the present invention.
Figure 27:
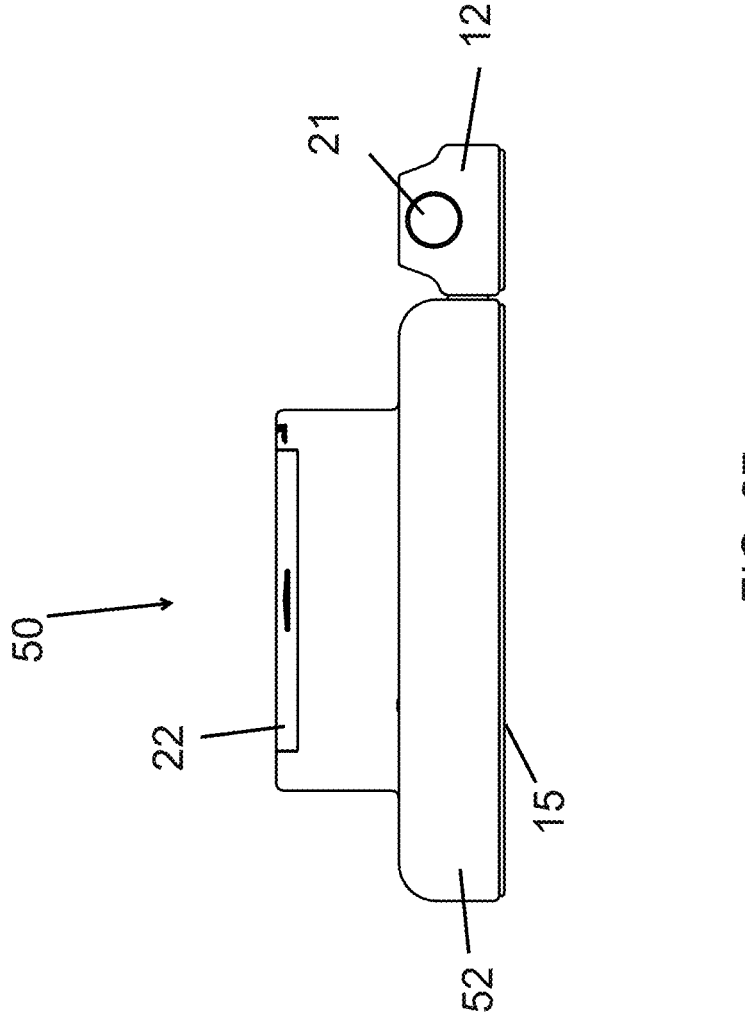
FIG. 27 is a top view of a fourth preferred embodiment of the apparatus of the present invention.
Figure 28:
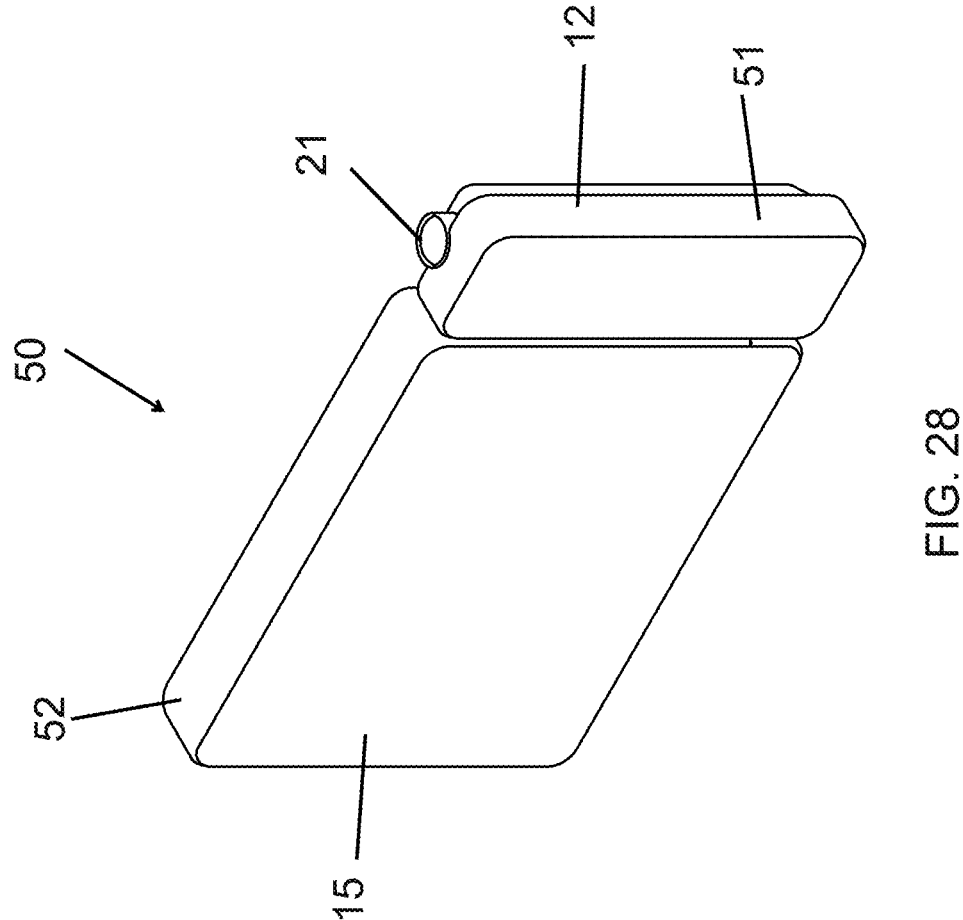
FIG. 28 is a perspective view of a fourth preferred embodiment of the apparatus of the present invention.
Figure 29:
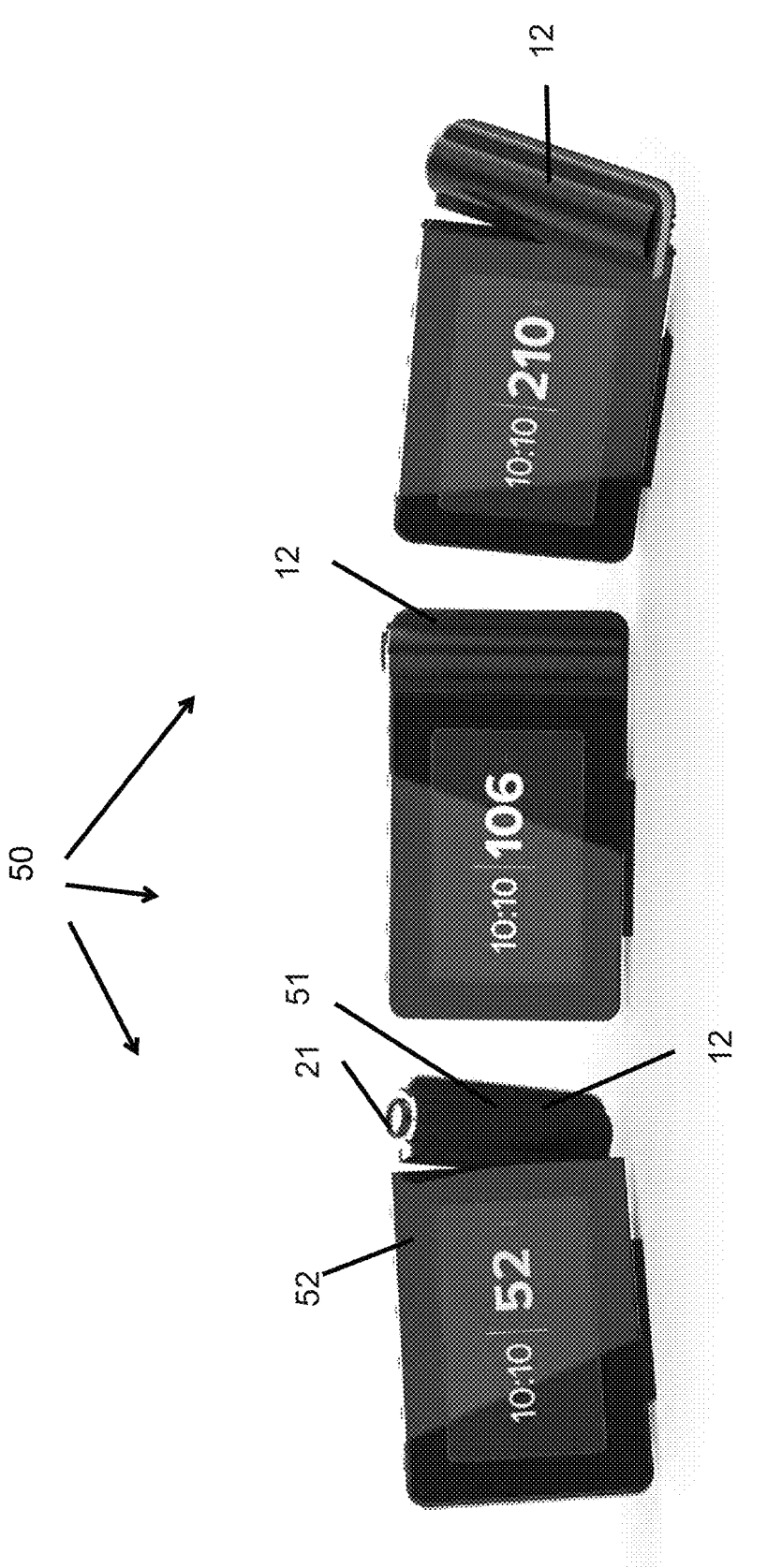
FIG. 29 illustrates a tilt function of projector in a fourth preferred embodiment of the apparatus of the present invention.

A projection device 50 can be the same or similar to a projection device 10, 30, 40 with the projector 12 of this embodiment coupled to a side of the device with a coupler 38 (see e.g., FIGS. 25, 31). Preferably coupler 38 enables projector 12 to tilt in forward and backward directions, as shown in FIG. 29, for example.

In different variations of this embodiment as shown in the figures, coupler 38 can be visible with a space between a housing 51 of projector 12 and a body 52 of projection device 50. Or a housing 51 of projector 12 and body 52 can be adjacent and close together with just enough space to enable the tilt motion but without seeing coupler 38 (see e.g., FIG. 92).

Also, preferably a lens 21 of projector 12 in projection device 50 is rotatable, and can be rotated for example by pressing switch 46. The views in FIGS. 23 to 96 also depict that various buttons and switches and ports (e.g., a projector on/off switch or button 17, a time set switch or button 16, a light adjustment switch or button 45, a rotation button 46, a USB charging port 18) can be on a back side of device 50. Various buttons and switches and ports (e.g., a projector on/off switch or button 17, a time set switch or button 16, a light adjustment switch or button 45, a rotation button 46, a USB charging port 18) can also be on a back side of devices 10, 30, 40, if desired.

Projection devices 10, 30, 40, 50 can each include one or more switches or buttons enabling adjustment of settings, e.g., a projector on/off switch or button 17, a time set switch or button 16, a light adjustment switch or button 45, which can be a dimmer slide for example. A projector on/off switch or button 17 can be adapted to turn on light beam 13 and to switch between different color or light intensity settings. A button or switch or knob 46 can also be included to rotate the image.

A projector 12 of device 10, 30, 40, 50 can be coupled in or to housing 11 or holder 32 so that its position can be manually adjusted. A switch or button or knob can also be included to adjust the position of projector 12 in housing 11 or holder 32, e.g., to cause projector 32 to tilt, or rotate or swivel as desired.

In one or more preferred embodiments of a device 10, 30, 40, 50, a lens 21 of a projector 12 can be adapted to rotate or swivel, while projector 12 is adapted to tilt in one or more desired directions.

In one or more preferred embodiments a position of a projector 12 can be manually adjusted, e.g., manually rotated, swiveled or tilted.

In one or more preferred embodiments a position of a projector 12 can be adjusted to rotate, swivel or tilt via a knob, button or switch.

In one or more preferred embodiments a position of a lens 21 of a projector 12 can be manually adjusted, e.g., manually rotated.

In one or more preferred embodiments a position of a lens 21 of a projector 12 can adjusted, e.g., rotated, using a knob or switch or button.

In one or more preferred embodiments, the software application on the electronic device is set to be continuously open so that it can continuously and automatically send information to a projection device 10, 30, 40, 50.

In one or more preferred embodiments, the software application on the electronic device is set to be open for a desired time interval so that it can continuously and automatically send information to a projection device 10, 30, 40, 50 during that time interval. In one or more preferred embodiments, the projection device 10, 30, 40, 50 can also be a smart device capable of having a software app.

In one or more preferred embodiments, the medical data projected is continuously and automatically updated to be the closest in time medical data received.

In one or more preferred embodiments, a software app receiving and/or transmitting data, e.g., glucose readings, can have a setting to stay open, or can be configured to always be open, to enable projected readings from the device to continuously and automatically be updated at desired time intervals.

In one or more preferred embodiments the wireless technology and the firmware or software of a projection device 10, 30, 40, 50 can be adapted to communicate with and/or receive data from a desired glucose software application on a smart device, e.g., an app sold under the trademarks Dexcom G5/6, Eversense, Guardian Connect, NutriSense or any other desired glucose monitoring related software application.

In one or more preferred embodiments the wireless technology and the firmware or software of a projection device 10, 30, 40 can be adapted to communicate with and/or receive data from a plurality of desired glucose software applications Dexcom G5/6, Eversense, Guardian Connect, NutriSense and any other desired glucose monitoring related software application, wherein the device can search for and determine which glucose related software application is nearby and available to connect with.

PARTS LIST

The following is a list of parts and materials suitable for use in the present invention:

| Parts Number | Description |
| --- | --- |
| 10 | apparatus/device of a preferred embodiment of the present invention, projection device, glucose reading projection device medical data projection device |
| 11 | body/base/housing |
| 12 | projector |
| 13 | light beam |
| 14 | top |
| 15 | screen/display |
| 16 | switch/button for time display |
| 17 | switch/button for projector display |
| 18 | charging port for electronic device/USB port |
| 19 | power cord |
| 20 | bottom |
| 21 | lens, focus lens |
| 22 | battery/battery backup |
| 23 | table/nightstand |
| 24 | time display/time |
| 25 | glucose reading display/medical data display/medical data/glucose reading |
| 26 | side, left side |
| 27 | front side |
| 28 | back side |
| 29 | side, right side |
| 30 | apparatus/device of a preferred embodiment of the present invention, projection device, glucose reading projection device |
| 31 | base/stand/housing |
| 32 | projector holder |
| 36 | arrow |
| 37 | phone |
| 38 | coupler, bracket, swivel or tilt bracket |
| 39 | wireless technology, e.g., Bluetooth ® technology |
| 40 | apparatus/device of a preferred embodiment of the present invention, projection device, glucose reading projection device medical data projection device |
| 41 | surface, ceiling |
| 42 | surface, wall |
| 43 | arrows |
| 44 | arrows |
| 45 | switch, button, dimmer, dimmer slide |
| 46 | button, switch, knob 46 for rotating image |
| 49 | firmware/software |
| 50 | apparatus/device of a preferred embodiment of the present invention, projection device, glucose reading projection device |

-continued

| Parts Number | Description |
| --- | --- |
| 51 | housing |
| 52 | body of apparatus 50 |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the claims.

The invention claimed is:

1. A system for projecting medical data of a patient comprising:

a) a first projection device that is a first receiver having a first housing, the first projection device able to receive data;

b) a second projection device that is a second receiver having a second housing, the second projection device also able to receive the data;

c) a first transmitter device that can receive the data and send the data to the first projection device, and a second transmitter device that can send the data to the second projection device;

d) the first transmitter device able to continuously and automatically send the data to the first projection device and able to continuously and automatically receive the data from a medical device;

e) the second projection device able to receive the data from the second transmitter when the first transmitter receives the data from the medical device;

f) the second transmitter device able to continuously and automatically send the data to the second projection device;

g) a first projector coupled to the first housing that projects a first light beam image of the data received by the first projection device onto a first desired surface that is spaced away from the first housing;

h) a second projector coupled to the second housing that projects a second light beam image of the data received by the second projection device onto a second desired surface that is spaced away from the second housing and in a different location from the first desired surface;

i) a first coupler that couples the first projector to the first housing;

j) a second coupler that couples the second projector to the second housing; and k) wherein the first light beam image of the data and the second light beam image of the data are each continuously and automatically updated to be most recent data from the medical device.

2. The system of claim 1 wherein the first projection device and the second projection device, are each able to continuously and automatically update the first light beam image and the second light beam image of the data.

3. The system of claim 2 wherein the second projection device and the first projection device are in different rooms of the same building and the first light beam image and the second light beam image are the same.

4. The system of claim 2 wherein the second projection device and the first projection device are in different cities and the first light beam image and the second light beam image are the same.

5. The system of claim 1 further comprising a third projection device that is also able to receive the data and to continuously and automatically update a third light beam image of the data.

6. The system of claim 5 wherein the third projection device, the second projection device, and the first projection device are in different rooms of the same building and the first light beam image, the second light beam image, and the third light beam image are the same.

7. The system of claim 5 wherein at least one of the third projection device, the second projection device, and the first projection device is in a different building from another said device.

8. The system of claim 5 wherein at least one of the third projection device, the second projection device, and the first projection device is in a different city from another said device.

9. The system of claim 1 wherein the first coupler enables the first projector to move so that a location of the first light beam image can be changed.

10. The system of claim 1 wherein the second coupler enables the second projector to move so that a location of the second light beam image can be changed.

11. The system of claim 9 wherein the second coupler enables the second projector to move so that a second location of the second light beam image can be changed.

12. The system of claim 1 wherein the first coupler enables the first projector to tilt and/or swivel and/or rotate so that a location of the first light beam image can be changed.

13. The system of claim 1 wherein the data includes glucose level data.

14. The system of claim 1, wherein the first projection device and/or the second projection device further comprises an alarm that is emitted if the data received by the first projection device and/or the second projection device, respectively, is not within a desired range.

15. The system of claim 14, wherein the first projection device and/or the second projection device further comprises an alert that is emitted when new data is received by the first projection device and/or the second projection device, respectively.

16. The system of claim 15, wherein the alert is different from the alarm.

17. The system of claim 1 wherein the first projection device and/or the second projection device is portable and sized to enable packing the first projection device and/or the second projection device, respectively, while traveling.

18. The system of claim 1 wherein the first projection device and/or the second projection device includes a screen to also display the data and/or other desired information.

19. The system of claim 1 wherein the first projection device and/or the second projection device includes a screen to also display the data and time.

20. The system of claim 1 wherein the first transmitter device is a smart phone or tablet.

* * * * *